(12) United States Patent
Ibrahim et al.

(10) Patent No.: US 8,642,606 B2
(45) Date of Patent: Feb. 4, 2014

(54) ZAP-70 ACTIVE COMPOUNDS

(75) Inventors: Prabha N. Ibrahim, Mountain View, CA (US); Chao Zhang, Moraga, CA (US)

(73) Assignee: Plexxikon Inc., Berkeley, CA (US)

( * ) Notice: Subject to any disclaimer, the term of this patent is extended or adjusted under 35 U.S.C. 154(b) by 0 days.

(21) Appl. No.: 13/244,071

(22) Filed: Sep. 23, 2011

(65) Prior Publication Data

US 2012/0077827 A1     Mar. 29, 2012

Related U.S. Application Data

(60) Provisional application No. 61/387,943, filed on Sep. 29, 2010.

(51) Int. Cl.
| | | |
|---|---|---|
| *A01N 43/90* | (2006.01) | |
| *A61K 31/519* | (2006.01) | |
| *C07D 487/00* | (2006.01) | |

(52) U.S. Cl.
USPC ........................................ 514/262.1; 544/262

(58) Field of Classification Search
None
See application file for complete search history.

(56) References Cited

FOREIGN PATENT DOCUMENTS

| WO | WO2006068760 | * | 6/2006 | ............ C07D 487/04 |
| WO | WO2009062118 | * | 5/2009 | ............ A61K 31/519 |

\* cited by examiner

*Primary Examiner* — Jeffrey Murray
(74) *Attorney, Agent, or Firm* — Sheppard Mullin Richter & Hampton LLP

(57) ABSTRACT

Compounds of Formula I:

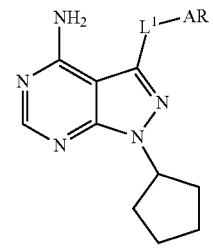

and salts thereof, formulations thereof, conjugates thereof, derivatives thereof, forms thereof and uses thereof are described. In certain aspects and embodiments, the described compounds or salts thereof, formulations thereof, conjugates thereof, derivatives thereof, forms thereof are active on one or more protein kinases, including a Zeta-chain-associated protein kinase 70 (ZAP-70), and any mutations thereof. Also described are methods of use thereof to treat diseases and conditions, including diseases and conditions associated with increased expression of ZAP-70 cancer, B-cell chronic lymphocytic leukemia, aggressive B-cell chronic lymphocytic leukemia, an allergy-related disease or an allergic inflammation.

8 Claims, No Drawings

ZAP-70 ACTIVE COMPOUNDS

RELATED PATENT APPLICATION

This application claims the benefit under 35 U.S.C §119(e) of U.S. Provisional Application No. 61/387,943 filed Sep. 29, 2010, entitled "ZAP-70 Active Compounds", which is incorporated herein by reference in its entirety and for all purposes.

FIELD OF THE INVENTION

Disclosed are compounds and uses thereof. In certain embodiments disclosed compounds are kinase inhibitors.

SUMMARY OF THE INVENTION

In certain aspects and embodiments disclosed herein, compounds are provided, as well as various salts thereof, formulations thereof, conjugates thereof, derivatives thereof, forms thereof and uses thereof. In some embodiments, compounds are of Formula I, Formula II, Formula III, Formula IV or Formula V as described below. In certain embodiments, the compounds are active on one or more protein kinases, including a Zeta-chain-associated protein kinase 70 (ZAP-70), and any mutations thereof. In certain embodiments, the compounds inhibit ZAP-70. In certain embodiments, the compounds inhibit ZAP-70 selectively to other protein kinases. In some embodiments, the compounds are active on a mutant ZAP-70. In some embodiments, the compounds inhibit a mutant ZAP-70. In some embodiments, the compounds are active on a mutant ZAP-70 having a M414A mutation. In some embodiments, the compounds inhibit a mutant ZAP-70 having a M414A mutation. In various aspects and embodiments, the compounds may be used to treat or prevent diseases associated with ZAP-70 kinase (or to prepare medicaments for such treatment or prevention). In some aspects and embodiments, the compounds may be used to treat or prevent diseases associated with increased expression of ZAP-70 kinase (or to prepare medicaments for such treatment or prevention). In some aspects and embodiments, the compounds may be used to treat or prevent a disease associated with ZAP-70 kinase mutations (or to prepare medicaments for such treatment or prevention). In some aspects and embodiments, the compounds may be used to treat or prevent a disease associated with a M414A ZAP-70 kinase mutation (or to prepare medicaments for such treatment or prevention). In some aspects and embodiments, the compounds may be used to treat or prevent a disease in a subject having a M414A ZAP-70 kinase mutation (or to prepare medicaments for such treatment or prevention). In some aspects and embodiments, the compounds may be used to treat or prevent cancer in a subject (or to prepare medicaments for such treatment or prevention). In some aspects and embodiments, the compounds may be used to treat or prevent B-cell chronic lymphocytic leukemia (CLL) (or to prepare medicaments for such treatment or prevention). In some aspects and embodiments, the compounds may be used to treat or prevent aggressive B-cell chronic lymphocytic leukemia (CLL) (or to prepare medicaments for such treatment or prevention). In some aspects and embodiments, the compounds may be used to treat or prevent B-cell chronic lymphocytic leukemia (CLL) in a subject exhibiting increased expression of ZAP-70 (or to prepare medicaments for such treatment or prevention). In some aspects and embodiments, the compounds may be used to treat or prevent an allergy-related disease in a subject (or to prepare medicaments for such treatment or prevention). In some aspects and embodiments, the compounds may be used to treat or prevent allergic inflammation in a subject (or to prepare medicaments for such treatment or prevention).

In one aspect, compounds having the structure according to the following Formula I are provided:

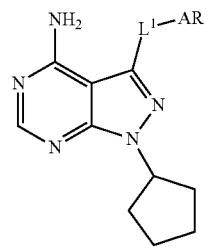

Formula I or a pharmaceutically acceptable salt thereof,
wherein:
$L^1$ is selected from the group consisting of lower alkylene, —O—, —CO—, $S(O)_2$ and —NH—; and
AR is a six membered aryl or heteroaryl ring substituted with one or more substituents selected from the group consisting of lower alkyl, lower alkoxy, and halogen;
provided, however, that the compound is not 1-cyclopentyl-3-(3-methylbenzyl)-1H-pyrazolo[3,4-d]pyrimidin-4-amine (hereinafter "CZ40").

In some embodiments of Formula I, $L^1$ is lower alkylene. In some embodiments of Formula I, $L^1$ is —O—. In some embodiments of Formula I, $L^1$ is —CO—. In some embodiments of Formula I, $L^1$ is $S(O)_2$. In some embodiments of Formula I, $L^1$ is —NH—. In some embodiments of Formula I, $L^1$ is methylene (provided that the compound is not CZ40).

In some embodiments of Formula I, AR is phenyl. In some embodiments of Formula I, AR is a six membered heteroaryl ring including at least one heteroatom. In some embodiments of Formula I, AR is a six membered heteroaryl ring including at least two heteroatoms. In some embodiments of Formula I, AR is a six membered heteroaryl ring including at least three heteroatoms. In some embodiments of Formula I, AR is a six membered heteroaryl ring including at least one nitrogen. In some embodiments of Formula I, AR is a six membered heteroaryl ring including at least one nitrogen in the 2-position. In some embodiments of Formula I, AR is a six membered heteroaryl ring including at least two nitrogens. In some embodiments of Formula I, AR is a six membered heteroaryl ring including at least three nitrogens.

In some embodiments of Formula I, AR is substituted with at least one substituent. In some embodiments of Formula I, AR is substituted with at least one substituent at a meta-position. In some embodiments of Formula I, AR is substituted with at least one substituent at an ortho-position. In some embodiments of Formula I, AR is substituted with at least two substituents. In some embodiments of Formula I, AR is substituted with at least two substituents with one substituent in a para-position and one substituent in a meta-position. In some embodiments of Formula I, the one or more substituents includes at least one methyl substituent. In some embodiments of Formula I, the one or more substituents includes at least one methoxy substituent. In some embodiments of Formula I, the one or more substituents includes at least one fluoro substituent. In some embodiments of Formula I, the one or more substituents includes at least one chloro substituent. In some embodiments of Formula I, the one or more substituents includes at least one bromo substituent. In some embodiments of Formula I, the one or more substituents includes at least one iodo substituent. In some embodiments of Formula I, the one or more substituents includes at least one substituent selected from the group consisting of methyl, methoxy, fluoro and chloro. In some embodiments of Formula I, the one or more substituents includes at least one substituent selected from the group consisting of methoxy, fluoro and chloro. In some embodiments of Formula I, the one or more substituents includes at least one fluoro or chloro substituent.

In one aspect, compounds having the structure according to the following Formula II are provided:

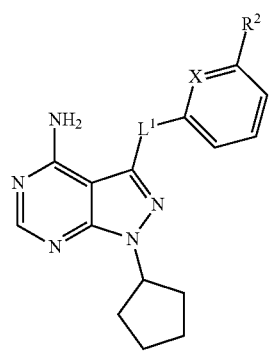

Formula II or a pharmaceutically acceptable salt thereof,
wherein:
X is CH or N;
$R^2$ is selected from the group consisting of lower alkyl, lower alkoxy, and halogen; and
$L^1$ is selected from the group consisting of lower alkylene, —O—, —CO—, $S(O)_2$ and —NH—;
provided, however, that if X is CH and $L^1$ is methylene, then $R^2$ is not methyl.

In some embodiments of Formula II, $R^2$ is methyl (provided that if $R^2$ is methyl, then $L^1$ is not methylene). In some embodiments of Formula II, $R^2$ is methoxy. In some embodiments of Formula II, $R^2$ is fluoro. In some embodiments of Formula II, $R^2$ is chloro. In some embodiments of Formula II, $R^2$ is bromo. In some embodiments of Formula II, $R^2$ is iodo. In some embodiments of Formula II, $R^2$ is selected from the group consisting of methyl, methoxy, fluoro and chloro (provided that if $R^2$ is methyl, then $L^1$ is not methyl). In some embodiments of Formula II, $R^2$ is selected from the group consisting of methyl, fluoro and chloro (provided that if $R^2$ is methyl, then $L^1$ is not methylene). In some embodiments of Formula II, $R^2$ is selected from the group consisting of methoxy, fluoro and chloro. In some embodiments of Formula II, $R^2$ is selected from the group consisting of fluoro and chloro.

In some embodiments of Formula II, $L^1$ is lower alkylene (provided that if $L^1$ is methylene, then $R^2$ is not methyl). In some embodiments of Formula II, $L^1$ is —O—. In some embodiments of Formula I, $L^1$ is —CO—. In some embodiments of Formula II, $L^1$ is $S(O)_2$. In some embodiments of Formula I, $L^1$ is —NH—. In some embodiments of Formula II, $L^1$ is methylene (provided that if $L^1$ is methylene, then $R^2$ is not methyl).

In one aspect, compounds having the structure according to the following Formula III are provided:

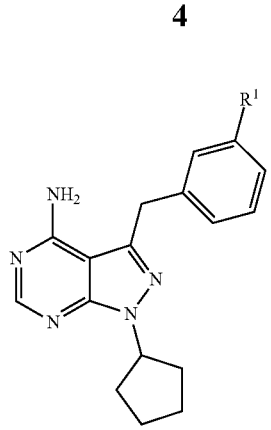

Formula III or a pharmaceutically acceptable salt thereof,
wherein:
$R^1$ is selected from the group consisting of lower alkoxy and halogen.

In some embodiments of Formula III, $R^1$ is methoxy. In some embodiments of Formula III, $R^1$ is fluoro. In some embodiments of Formula III, $R^1$ is chloro. In some embodiments of Formula III, $R^1$ is bromo. In some embodiments of Formula III, $R^1$ is iodo. In some embodiments of Formula III, $R^1$ is selected from the group consisting of methoxy, fluoro and chloro. In some embodiments of Formula III, $R^1$ is selected from the group consisting of fluoro and chloro.

In one aspect, compounds having the structure according to the following Formula IV are provided:

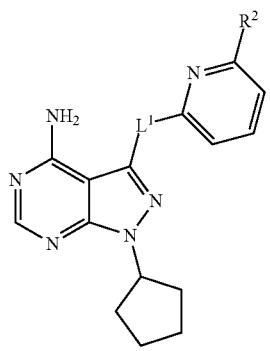

Formula IV or a pharmaceutically acceptable salt thereof,
wherein:
$R^2$ is selected from the group consisting of lower alkyl, lower alkoxy, and halogen; and
$L^1$ is selected from the group consisting of lower alkylene, —O—, —CO—, $S(O)_2$ and —NH—.

In some embodiments of Formula IV, $R^2$ is methyl. In some embodiments of Formula IV, $R^2$ is methoxy. In some embodiments of Formula IV, $R^2$ is fluoro. In some embodiments of Formula IV, $R^2$ is chloro. In some embodiments of Formula IV, $R^2$ is bromo. In some embodiments of Formula IV, $R^2$ is iodo. In some embodiments of Formula IV, $R^2$ is selected from the group consisting of methyl, methoxy, fluoro and chloro. In some embodiments of Formula IV, $R^2$ is selected from the group consisting of methyl, fluoro and chloro. In some embodiments of Formula IV, $R^2$ is selected from the group consisting of fluoro and chloro.

In some embodiments of Formula IV, $L^1$ is lower alkylene. In some embodiments of Formula IV, $L^1$ is —O—. In some embodiments of Formula IV, L¹ is —CO—. In some embodiments of Formula IV, L¹ is S(O)₂. In some embodiments of Formula IV, L¹ is —NH—. In some embodiments of Formula IV, L¹ is methylene.

In one aspect, compounds having the structure according to the following Formula V are provided:

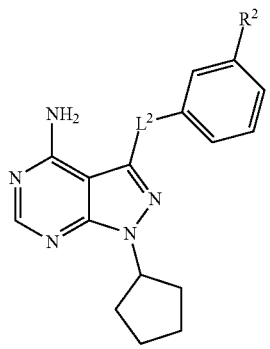

Formula V or a pharmaceutically acceptable salt thereof,
wherein:
R² is selected from the group consisting of lower alkyl, lower alkoxy, and halogen; and
L² is selected from the group consisting of —O—, —CO—, S(O)₂ and —NH—.

In some embodiments of Formula V, R² is methyl. In some embodiments of Formula V, R² is methoxy. In some embodiments of Formula V, R² is fluoro. In some embodiments of Formula V, R² is chloro. In some embodiments of Formula V, R² is bromo. In some embodiments of Formula V, R² is iodo. In some embodiments of Formula V, R² is selected from the group consisting of methyl, methoxy, fluoro and chloro. In some embodiments of Formula V, R² is selected from the group consisting of methyl, fluoro and chloro. In some embodiments of Formula V, R² is selected from the group consisting of fluoro and chloro.

In some embodiments of Formula V, L² is —O—. In some embodiments of Formula V, L² is —CO—. In some embodiments of Formula V, L² is S(O)₂. In some embodiments of Formula V, L² is —NH—.

In one aspect, a compound having the structure according to the following Compound 1a (3-(3-chlorobenzyl)-1-cyclopentyl-1H-pyrazolo[3,4-d]pyrimidin-4-amine) is provided:

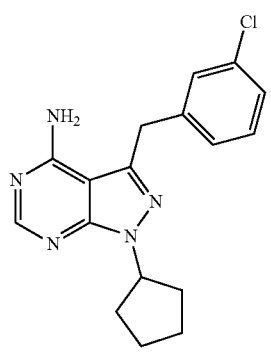

Compound 1a or a pharmaceutically acceptable salt thereof.

In one aspect, a compound having the structure according to the following Compound 1b (1-cyclopentyl-3-(3-fluorobenzyl)-1H-pyrazolo[3,4-d]pyrimidin-4-amine) is provided:

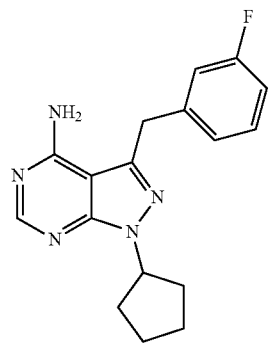

Compound 1b or a pharmaceutically acceptable salt thereof.

In one aspect, a compound having the structure according to the following Compound 1c (1-cyclopentyl-3-(3-methoxybenzyl)-1H-pyrazolo[3,4-d]pyrimidin-4-amine) is provided:

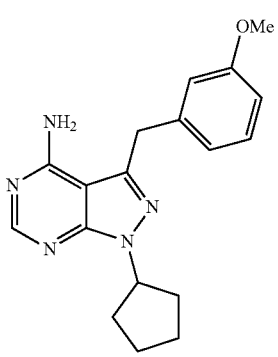

Compound 1c or a pharmaceutically acceptable salt thereof.

In one aspect, a compound having the structure according to the following Compound 2a (1-cyclopentyl-3-((6-methylpyridin-2-yl)methyl)-1H-pyrazolo[3,4-d]pyrimidin-4-amine) is provided:

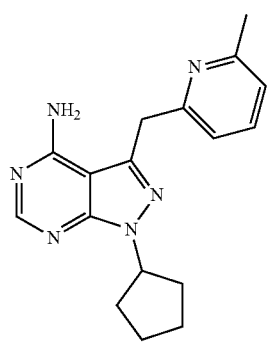

Compound 2a or a pharmaceutically acceptable salt thereof.

In one aspect, a compound having the structure according to the following Compound 2b (3-((6-chloropyridin-2-yl)methyl)-1-cyclopentyl-1H-pyrazolo[3,4-d]pyrimidin-4-amine) is provided:

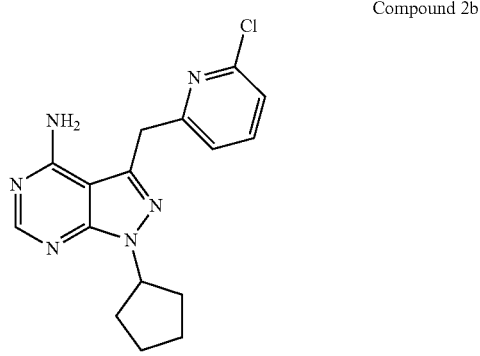 [SMILES: Nc1ncnc2c1c(Cc1cccc(Cl)n1)nn2C1CCCC1]

Compound 2b or a pharmaceutically acceptable salt thereof.

In one aspect, a compound having the structure according to the following Compound 2c (1-cyclopentyl-3-((6-fluoropyridin-2-yl)methyl)-1H-pyrazolo[3,4-d]pyrimidin-4-amine) is provided:

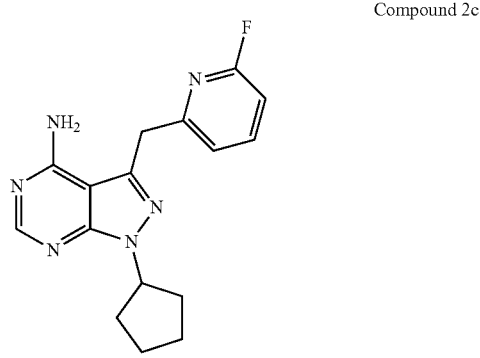 [SMILES: Nc1ncnc2c1c(Cc1cccc(F)n1)nn2C1CCCC1]

Compound 2c or a pharmaceutically acceptable salt thereof.

In one aspect, a compound having the structure according to the following Compound 2d (1-cyclopentyl-34(6-methoxypyridin-2-yl)methyl)-1H-pyrazolo[3,4-d]pyrimidin-4-amine) is provided:

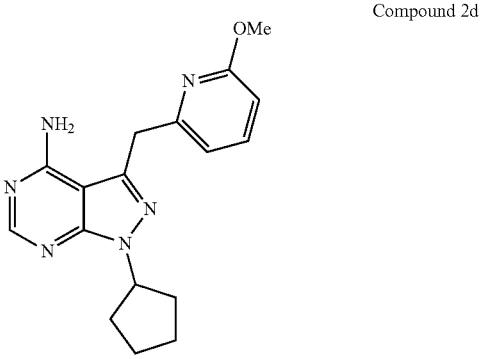 [SMILES: COc1cccc(Cc2nn(C3CCCC3)c3ncnc(N)c23)n1]

Compound 2d or a pharmaceutically acceptable salt thereof.

In one aspect, a compound having the structure according to the following Compound 3a (1-cyclopentyl-$N^3$-m-tolyl-1H-pyrazolo[3,4-d]pyrimidine-3,4-diamine) is provided:

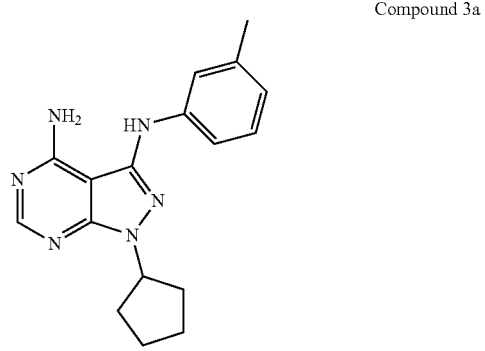 [SMILES: Cc1cccc(Nc2nn(C3CCCC3)c3ncnc(N)c23)c1]

Compound 3a or a pharmaceutically acceptable salt thereof.

In one aspect, a compound having the structure according to the following Compound 3b ($N^3$-(3-chlorophenyl)-1-cyclopentyl-1H-pyrazolo[3,4-d]pyrimidine-3,4-diamine) is provided:

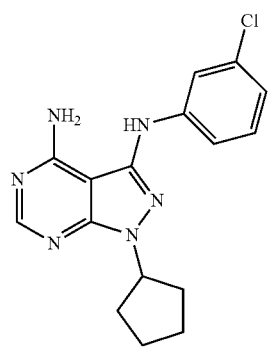

Compound 3b or a pharmaceutically acceptable salt thereof.

In one aspect, a compound having the structure according to the following Compound 3c (1-cyclopentyl-$N^3$-(3-fluorophenyl)-1H-pyrazolo[3,4-d]pyrimidine-3,4-diamine) is provided:

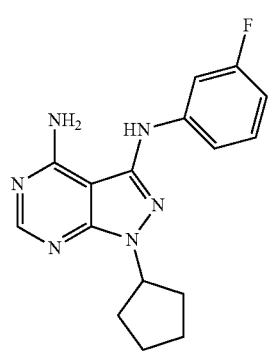

Compound 3c or a pharmaceutically acceptable salt thereof.

In one aspect, a compound having the structure according to the following Compound 3d (1-cyclopentyl-N³-(3-methoxyphenyl)-1H-pyrazolo[3,4-d]pyrimidine-3,4-diamine) is provided:

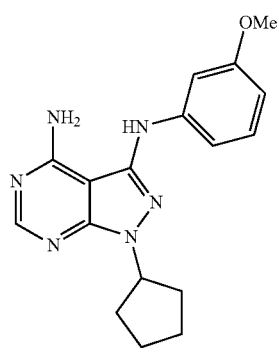

Compound 3d or a pharmaceutically acceptable salt thereof.

In one aspect, a compound having the structure according to the following Compound 4a (1-cyclopentyl-3-(m-tolyloxy)-1H-pyrazolo[3,4-d]pyrimidin-4-amine) is provided:

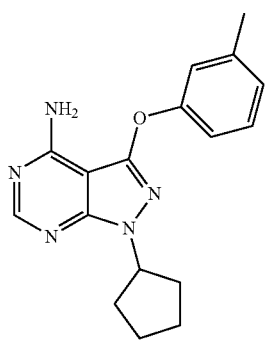

Compound 4a or a pharmaceutically acceptable salt thereof.

In one aspect, a compound having the structure according to the following Compound 4b (3-(3-chlorophenoxy)-1-cyclopentyl-1H-pyrazolo[3,4-d]pyrimidin-4-amine) is provided:

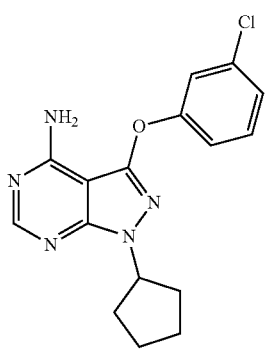

Compound 4b or a pharmaceutically acceptable salt thereof.

In one aspect, a compound having the structure according to the following Compound 4c (1-cyclopentyl-3-(3-fluorophenoxy)-1H-pyrazolo[3,4-d]pyrimidin-4-amine) is provided:

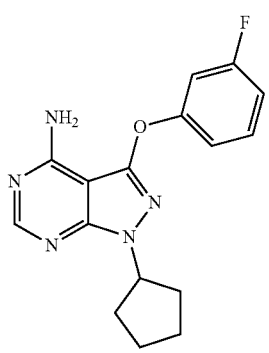

Compound 4c or a pharmaceutically acceptable salt thereof.

In one aspect, a compound having the structure according to the following Compound 4d (1-cyclopentyl-3-(3-methoxyphenoxy)-1H-pyrazolo[3,4-d]pyrimidin-4-amine) is provided:

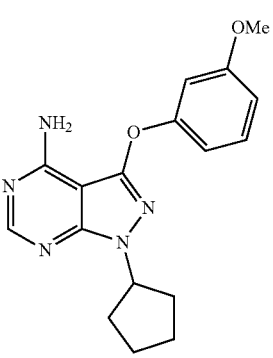

Compound 4d or a pharmaceutically acceptable salt thereof.

In one aspect, a compound having the structure according to the following Compound 5a ((4-amino-1-cyclopentyl-1H-pyrazolo[3,4-d]pyrimidin-3-yl)(m-tolyl)methanone) is provided:

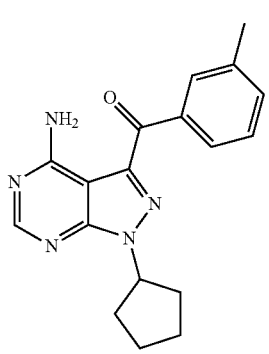

Compound 5a or a pharmaceutically acceptable salt thereof.

In one aspect, a compound having the structure according to the following Compound 5b ((4-amino-1-cyclopentyl-1H-pyrazolo[3,4-d]pyrimidin-3-yl)(3-chlorophenyl)methanone) is provided:

Compound 5b

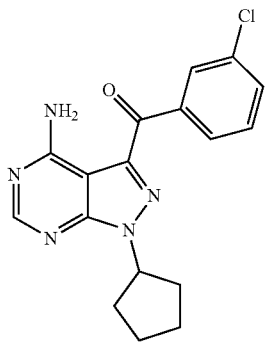

or a pharmaceutically acceptable salt thereof.

In one aspect, a compound having the structure according to the following Compound 5c ((4-amino-1-cyclopentyl-1H-pyrazolo[3,4-d]pyrimidin-3-yl)(3-fluorophenyl)methanone) is provided:

Compound 5c

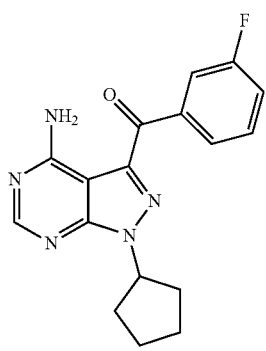

In one aspect, a compound having the structure according to the following Compound 5d ((4-amino-1-cyclopentyl-1H-pyrazolo[3,4-d]pyrimidin-3-yl)(3-methoxyphenyl)methanone) is provided:

Compound 5d

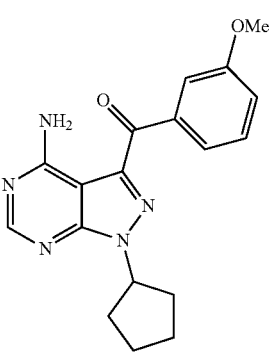

or a pharmaceutically acceptable salt thereof.

Accordingly, in a $1^{st}$ set of embodiments, the invention provides a compound having the chemical structure of Formula I,

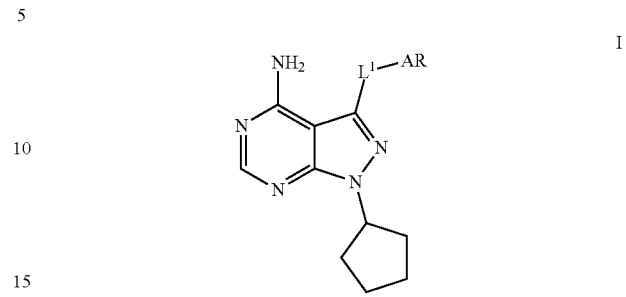

I or a pharmaceutically acceptable salt thereof, wherein: $L^1$ is selected from the group consisting of lower alkylene, —O—, —CO—, $S(O)_2$ and —NH—; and AR is a six membered aryl or heteroaryl ring substituted with one or more substituents selected from the group consisting of lower alkyl, lower alkoxy, and halogen; provided, however, that the compound is not 1-cyclopentyl-3-(3-methylbenzyl)-1H-pyrazolo[3,4-d]pyrimidin-4-amine (hereinafter "CZ40").

In a $2^{nd}$ set of embodiments, the invention provides compounds of set 1, wherein $L^1$ is lower alkylene, —O—, —CO—. $S(O)_2$, —NH_or methylene.

In a $3^{rd}$ set of embodiments, the invention provides compounds of any of set 1 or 2, wherein AR is a six membered heteroaryl ring comprising at least one heteroatom, a six membered heteroaryl ring comprising at least two heteroatoms, a six membered heteroaryl ring comprising at least three heteroatoms, a six membered heteroaryl ring comprising at least one nitrogen, a six membered heteroaryl ring including at least two nitrogens, a six membered heteroaryl ring including at least three nitrogens, or a six membered heteroaryl ring including at least one nitrogen in the 2-position.

In a $4^{th}$ set of embodiments, the invention provides compounds of any of set 1, 2 or 3, wherein AR is substituted with at least one substituent, AR is substituted with at least one substituent at a meta-position, or AR is substituted with at least one substituent at an ortho-position.

In a $5^{th}$ set of embodiments, the invention provides compounds of any of set 1, 2, 3 or 4, wherein AR is substituted with at least one substituent, AR is substituted with at least one substituent at a meta-position, AR is substituted with at least one substituent at an ortho-position, AR is substituted with at least two substituents, or AR is substituted with at least two substituents with one substituent in a para-position and one substituent in a meta-position.

In a $6^{th}$ set of embodiments, the invention provides compounds of any of set 1, 2, 3, 4 or 5, wherein one or more substituents comprise at least one methyl substituent, one or more substituents comprise at least one methoxy substituent, one or more substituents comprise at least one fluoro substituent, one or more substituents comprise at least one chloro substituent, one or more substituents comprise at least one bromo substituent, one or more substituents comprise at least one bromo substituent, one or more substituents comprise at least one iodo substituent, one or more substituents comprise at least one substituent selected from the group consisting of methoxy, fluoro and chloro, or one or more substituents comprise at least one fluoro or chloro substituent.

In a $7^{th}$ set of embodiments, the invention provides compounds having formula II:

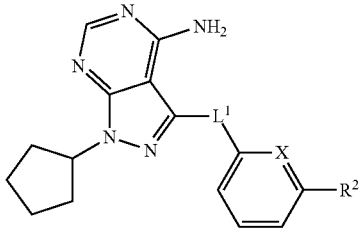

II or a pharmaceutically acceptable salt thereof, wherein X is C or N; $R^2$ is selected from the group consisting of lower alkyl, lower alkoxy, and halogen; and $L^1$ is selected from the group consisting of lower alkylene, —O—, —CO—, S(O)$_2$ and —NH—; provided, however, that if X is C and $L^1$ is methylene, then $R^2$ is not methyl.

In an 8$^{th}$ set of embodiments, the invention provides compounds having formula III:

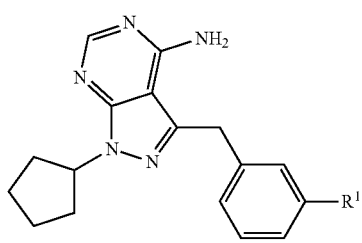

III or a pharmaceutically acceptable salt thereof, wherein $R^1$ is selected from the group consisting of lower alkoxy and halogen.

In a 9$^{th}$ set of embodiments, the invention provides compounds having formula IV:

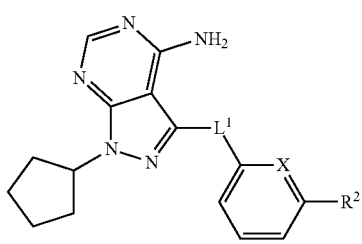

IV or a pharmaceutically acceptable salt thereof, wherein $R^2$ is selected from the group consisting of lower alkyl, lower alkoxy, and halogen; and $L^1$ is selected from the group consisting of lower alkylene, —O—, —CO—, S(O)$_2$ and —NH—.

In a 10$^{th}$ set of embodiments, the invention provides compounds having Formula V:

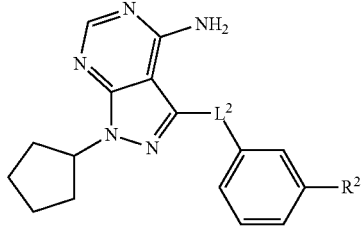

V or a pharmaceutically acceptable salt thereof, wherein $R^2$ is selected from the group consisting of lower alkyl, lower alkoxy, and halogen; and $L^2$ is selected from the group consisting of —O—, —CO—, S(O)$_2$ and —NH—.

In an 11$^{th}$ set of embodiments, the invention provides compounds of any of set 1, 2, 3, 4, 5, 6, 7, 8, 9 or 10, wherein $R^1$, if present, is methoxy, F, Cl, Br, I, or selected from the group consisting of methoxy, fluoro and chloro, or selected from the group consisting of fluoro and chloro.

In a 12$^{th}$ set of embodiments, the invention provides compounds of any of set 1, 2, 3, 4, 5, 6, 7, 8, 9, 10 or 11, wherein $R^2$, if present, is methyl, methoxy, F, Cl, Br, I, or selected from the group consisting of methoxy, fluoro and chloro, or selected from the group consisting of fluoro and chloro.

In a 13$^{th}$ set of embodiments, the invention provides compounds of any of set 1, 2, 3, 4, 5, 6, 7, 8, 9, 10 11 or 12, wherein $L^1$, if present, is lower alkylene, O, —CO—, SO$_2$, NH, or methylene.

In a 14$^{th}$ set of embodiments, the invention provides compounds of any of set 1, 2, 3, 4, 5, 6, 7, 8, 9, 10 11, 12 or 13, wherein $L^2$, if present, is O, —CO—, SO$_2$, or NH.

In a 15$^{th}$ set of embodiments, the invention provides compounds of any of set 1, 2, 3, 4, 5, 6, 7, 8, 9, 10 11, 12, 13 or 14, wherein X is C or N.

In a 16$^{th}$ set of embodiments, the invention provides a compound or a pharmaceutically acceptable salt thereof, wherein the compound is (3-(3-chlorobenzyl)-1-cyclopentyl-1H-pyrazolo[3,4-d]pyrimidin-4-amine), (1-cyclopentyl-3-(3-fluorobenzyl)-1H-pyrazolo[3,4-d]pyrimidin-4-amine), (1-cyclopentyl-3-(3-methoxybenzyl)-1H-pyrazolo[3,4-d]pyrimidin-4-amine), (1-cyclopentyl-3-((6-methylpyridin-2-yl)methyl)-1H-pyrazolo[3,4-d]pyrimidin-4-amine), (34(6-chloropyridin-2-yl)methyl)-1-cyclopentyl-1H-pyrazolo[3,4-d]pyrimidin-4-amine), (1-cyclopentyl-3-((6-fluoropyridin-2-yl)methyl)-1H-pyrazolo[3,4-d]pyrimidin-4-amine), (1-cyclopentyl-3-((6-methoxypyridin-2-yl)methyl)-1H-pyrazolo[3,4-d]pyrimidin-4-amine), (1-cyclopentyl-$N^3$-m-tolyl-1H-pyrazolo[3,4-d]pyrimidine-3,4-diamine), ($N^3$-(3-chlorophenyl)-1-cyclopentyl-1H-pyrazolo[3,4-d]pyrimidine-3,4-diamine), (1-cyclopentyl-$N^3$-(3-fluorophenyl)-1H-pyrazolo[3,4-d]pyrimidine-3,4-diamine), (1-cyclopentyl-$N^3$-(3-methoxyphenyl)-1H-pyrazolo[3,4-d]pyrimidine-3,4-diamine), (1-cyclopentyl-3-(m-tolyloxy)-1H-pyrazolo[3,4-d]pyrimidin-4-amine), (3-(3-chlorophenoxy)-1-cyclopentyl-1H-pyrazolo[3,4-d]pyrimidin-4-amine), (1-cyclopentyl-3-(3-fluorophenoxy)-1H-pyrazolo[3,4-d]pyrimidin-4-amine), (1-cyclopentyl-3-(3-methoxyphenoxy)-1H-pyrazolo[3,4-d]pyrimidin-4-amine), ((4-amino-1-cyclopentyl-1H-pyrazolo[3,4-d]pyrimidin-3-yl)(m-toly)methanone), ((4-amino-1-cyclopentyl-1H-pyrazolo[3,4-d]pyrimidin-3-yl)(3-chlorophenyl)methanone), or ((4-amino-1-cyclopentyl-1H-pyrazolo[3,4-d]pyrimidin-3-yl)(3-fluorophenyl)methanone).

In a 17$^{th}$ set of embodiments, the invention provides a composition, wherein the composition comprises a compound of any of set 1, 2, 3, 4, 5, 6, 7, 8, 9, 10 11, 12, 13, 14, 15 or 16, and a pharmaceutically acceptable carrier.

In an 18<sup>th</sup> set of embodiments, the invention provides a kit, wherein the kit comprises a compound of any of set 1, 2, 3, 4, 5, 6, 7, 8, 9, 10 11, 12, 13, 14, 15 or 16 or a composition of set 17.

In a 19<sup>th</sup> set of embodiments, the invention provides a compound of any of set 1, 2, 3, 4, 5, 6, 7, 8, 9, 10 11, 12, 13, 14, 15 or 16, or a composition of set 17, wherein the composunt or composition is active on one or more protein kinase. In some embodiments, the compound or composition of set 19 is active on Zeta-chain-associated protein kinase 70 (ZAP-70), and/or any mutations thereof. In other embodiments, the compound or composition of set 19 inhibits ZAP-70. In yet other embodiments, the compound or composition of set 19 active on a mutant ZAP-70. In still other embodiments, the compound or composition of set 19 inhibits a mutant ZAP-70. In some embodiments, the compound or composition of set 19 is active on a mutant ZAP-70 having a M414A mutation. In other embodiments, the compound or composition of set 19 inhibits a mutant ZAP-70 having a M414A mutation.

In a 20<sup>th</sup> set of embodiments, the invention provides a method for treating or preventing a disease or condition associated with ZAP-70 kinase. The method includes administering to a subject in need thereof or suffering from the disease or condition an effective amount of a compound or composition of set 19.

In a 21<sup>st</sup> set of embodiments, the invention provides a method for treating or preventing a disease or condition associated with increased expression of ZAP-70. The method includes administering to a subject in need thereof or suffering from the disease or condition an effective amount of a compound or composition of set 19.

In a 22<sup>nd</sup> set of embodiments, the invention provides a method for treating or preventing a disease or condition associated with ZAP-70 kinase mutations. The method includes administering to a subject in need thereof or suffering from the disease or condition an effective amount of a compound or composition of set 19.

In a 23<sup>rd</sup> set of embodiments, the invention provides a method for treating or preventing a disease or condition in a subject having a M414A ZAP-70 kinase mutation. The method includes administering to the subject in need thereof or suffering from the disease or condition an effective amount of a compound or composition of set 19.

In a 24<sup>th</sup> set of embodiments, the invention provides a method for treating or preventing a cancer. The method includes administering to the subject in need thereof or suffering from the cancer an effective amount of a compound or composition of set 19.

In a 25<sup>th</sup> set of embodiments, the invention provides a method for treating or preventing a disease or condition selected from B-cell chronic lymphocytic leukemia (CLL), aggressive B-cell chronic lymphocytic leukemia (CLL), B-cell chronic lymphocytic leukemia (CLL), an allergy-related disease or allergic inflammation. The method includes administering to the subject in need thereof or suffering from the disease or condition an effective amount of a compound or composition of set 19.

In one embodiment of any of the above aspects and embodiments, the compound includes any tautomer thereof.

In one embodiment of any of the above aspects and embodiments, the compound includes any stereoisomer thereof.

In one embodiment of any of the above aspects and embodiments, the compound includes any pharmaceutically acceptable formulation thereof.

In one embodiment of any of the above aspects and embodiments, the compound includes any conjugate thereof.

In one embodiment of any of the above aspects and embodiments, the compound includes any derivative thereof.

In one embodiment of any of the above aspects and embodiments, the compound includes any form thereof.

In reference to compounds described herein, unless clearly indicated to the contrary, specification of a compound or group of compounds includes salts of such compound(s) (including pharmaceutically acceptable salts), formulations of such compound(s) (including pharmaceutically acceptable formulations), conjugates thereof, derivatives thereof, forms thereof, prodrugs thereof, and all stereoisomers thereof. In reference to compositions, kits, methods of use, etc. of compounds as described herein, i.e. compounds of the invention, it is understood (unless indicated otherwise) that a compound as described herein includes compounds of Formula I, Formula II, Formula III, Formula III, Formula IV, Formula V including all sub-embodiments thereof, compounds of Formula II including all sub-embodiments thereof, and compounds as listed in the third aspect above, including all sub-embodiments thereof.

In one aspect, methods are provided for treating any protein kinase mediated disease or condition in an animal subject in need thereof, wherein the method involves administering to the subject an effective amount of any one or more compound (s) as described herein. In certain embodiments, the method involves administering to the subject an effective amount of any one or more compound(s) as described herein in combination with one or more other therapies for the disease or condition.

In one aspect, a compound as described herein is a ZAP-70 inhibitor and has an $IC_{50}$ of less than 500 nM, less than 100 nM, less than 50 nM, less than 20 nM, less than 10 nM, less than 5 nM, or less than 1 nM as determined in a ZAP-70 kinase activity assay. In some embodiments, a compound as described herein will selectively inhibit ZAP-70 kinase relative to one or more other non-ZAP-70 kinases.

In one aspect, compositions are provided that include a therapeutically effective amount of any one or more compound(s) as described herein and at least one pharmaceutically acceptable carrier, excipient, and/or diluent, including combinations of any two or more compounds as described herein. The composition can further include a plurality of different pharmacologically active compounds, which can include a plurality of compounds as described herein. In certain embodiments, the composition can include any one or more compound(s) as described herein along with one or more compounds that are therapeutically effective for the same disease indication. In one embodiment, the composition includes any one or more compound(s) as described herein along with one or more compounds that are therapeutically effective for the same disease indication, wherein the compounds have a synergistic effect on the disease indication. In one embodiment, the composition includes any one or more compound(s) as described herein effective in treating a cancer and one or more other compounds that are effective in treating the same cancer, further wherein the compounds are synergistically effective in treating the cancer.

In a one aspect, the invention provides methods for treating a disease or condition mediated by ZAP-70, including mutations thereof, in a subject in need thereof by administering to the subject an effective amount of a composition including any one or more compound(s) as described herein. In one embodiment, the invention provides methods for treating a disease or condition mediated by ZAP-70, including mutations thereof, by administering to the subject an effective amount of a composition including any one or more compound(s) as described herein in combination with one or more other suitable therapies for treating the disease.

In one aspect, the invention provides a method of treating a cancer in a subject in need thereof by administering to the subject an effective amount of a composition including any one or more compound(s) as described herein. In one embodiment, the invention provides a method of treating a cancer in a subject in need thereof by administering to the subject an effective amount of a composition including any one or more compound(s) as described herein in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, γ-ray, or electron, proton, neutron, or α particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), surgery, or bone marrow and stem cell transplantation.

In one aspect, the invention provides a method of treating a cancer in a subject in need thereof by administering to the subject an effective amount of a composition including any one or more compound(s) as described herein in combination with one or more suitable chemotherapeutic agents. In one embodiment, the one or more suitable chemotherapeutic agents is selected from an alkylating agent, including, but not limited to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosphamide, and uramustine; an antibiotic, including, but not limited to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limited to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, azathioprine, raltitrexed, tegafur-uracil, thioguanine, trimethoprim, trimetrexate, and vidarabine; an immunotherapy, including, but not limited to, alemtuzumab, bevacizumab, cetuximab, galiximab, gemtuzumab, panitumumab, pertuzumab, rituximab, tositumomab, trastuzumab, 90Y ibritumomab tiuxetan, ipilimumab, and tremelimumab; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, larotaxel, ortataxel, paclitaxel, DHA-paclitaxel, and tesetaxel; a retinoid, including, but not limited to, alitretinoin, bexarotene, fenretinide, isotretinoin, and tretinoin; an alkaloid, including, but not limited to, demecolcine, homoharringtonine, vinblastine, vincristine, vindesine, vinflunine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not limited to, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), and vatalanib; a targeted signal transduction inhibitor including, but not limited to bortezomib, geldanamycin, and rapamycin; a biological response modifier, including, but not limited to, imiquimod, interferon-α, and interleukin-2; and other chemotherapeutics, including, but not limited to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. temsirolimus, everolimus, deforolimus), PI3K inhibitors (e.g. BEZ235, GDC-0941, XL147, XL765), Cdk4 inhibitors (e.g. PD-332991), Akt inhibitors, Hsp90 inhibitors (e.g. tanespimycin) and farnesyltransferase inhibitors (e.g. tipifarnib). Preferably, the method of treating a cancer involves administering to the subject an effective amount of a composition including any one or more compound(s) as described herein in combination with a chemotherapeutic agent selected from capecitabine, 5-fluorouracil, carboplatin, dacarbazine, gefitinib, oxaliplatin, paclitaxel, SN-38, temozolomide, vinblastine, bevacizumab, cetuximab, interferon-α, interleukin-2, or erlotinib.

In a one aspect, the invention provides a method of treating a disease or condition in a subject in need thereof, by administering to the subject a therapeutically effective amount of any one or more compound(s) as described herein, a prodrug of such compound, a pharmaceutically acceptable salt of such compound or prodrug, or a pharmaceutically acceptable formulation of such compound or prodrug. The compound can be alone or can be part of a composition. In one embodiment, the invention provides a method of treating a disease or condition in a subject, by administering to the subject a therapeutically effective amount of any one or more compound(s) as described herein, a prodrug of such compound, a pharmaceutically acceptable salt of such compound or prodrug, or a pharmaceutically acceptable formulation of such compound or prodrug in combination with one or more other suitable therapies for the disease or condition.

In one aspect, the invention provides kits that include a compound or composition thereof as described herein. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a protein kinase mediated disease or condition; the invention kit includes written instructions for use and/or other indication that the compound or composition is suitable or approved for administration to a mammal, e.g., a human, for a ZAP-70-mediated disease or condition; and the compound or composition is packaged in unit dose or single dose form, e.g., single dose pills, capsules, or the like.

In aspects and embodiments involving treatment of a disease or condition with any one or more compound(s) as described herein, in a subject in need thereof (e.g. a mammal such as a human, other primates, sports animals, animals of commercial interest such as cattle, farm animals such as horses, or pets such as dogs and cats). In one embodiment, the disease is selected from the group consisting of neurologic diseases, including, but not limited to, multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma, sarcoma, carcinoma (e.g. gastrointestinal, liver, biliary tract, bile duct (cholangiocarcinoma), colorectal, lung, gallbladder, breast, pancreatic, thyroid, renal, ovarian, adrenocortical, prostate), lymphoma (e.g. histiocytic lymphoma) neurofibromatosis, gastrointestinal stromal tumors, acute myeloid leukemia, myelodysplastic syndrome, leukemia, tumor angiogenesis, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori, Hepatitis and Influenza* viruses, fever, HIV, and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency). In one embodiment, the disease or condition is selected from the group consisting of melanoma, glioma, glioblastoma multiforme, pilocytic astrocytoma, sarcoma, liver cancer, biliary tract cancer, cholangiocarcinoma, colorectal cancer, lung cancer, gallbladder cancer, breast cancer, pancreatic cancer, thyroid cancer, renal cancer, ovarian cancer, adrenocortical cancer, prostate cancer, histiocytic lymphoma, neurofibromatosis, gastrointestinal stromal tumors, acute myeloid leukemia, myelodysplastic syndrome, leukemia, tumor angiogenesis, medullary thyroid cancer, carcinoid, small cell lung cancer, Kaposi's sarcoma, pheochromocytoma, acute pain, chronic pain, and polycystic kidney disease. In a preferred embodiment, the disease or condition is selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, cholangiocarcinoma, acute pain, chronic pain, and polycystic kidney disease.

Additional aspects and embodiments will be apparent from the following Detailed Description of the Invention and from the claims.

DETAILED DESCRIPTION OF THE INVENTION

As used herein the following definitions apply unless clearly indicated otherwise:

All atoms designated within a Formula described herein, either within a structure provided, or within the definitions of variables related to the structure, is intended to include any isotope thereof, unless clearly indicated to the contrary. It is understood that for any given atom, the isotopes may be present essentially in ratios according to their natural occurrence, or one or more particular atoms may be enhanced with respect to one or more isotopes using synthetic methods known to one skilled in the art. Thus, hydrogen includes for example $^{1}H$, $^{2}H$, $^{3}H$; carbon includes for example $^{11}C$, $^{12}C$, $^{13}C$, $^{14}C$; oxygen includes for example nitrogen includes for example $^{13}N$, $^{14}N$, $^{15}N$; sulfur includes for example $^{32}S$, $^{33}S$, $^{34}S$, $^{35}S$, $^{36}S$, $^{37}S$, $^{38}S$; fluoro includes for example $^{17}F$, $^{18}F$, $^{19}F$; chloro includes for example $^{35}Cl$, $^{36}Cl$, $^{37}Cl$, $^{38}Cl$, $^{39}Cl$; and the like.

"Halogen" refer to all halogens, that is, chloro (Cl), fluoro (F), bromo (Br), or iodo (I).

"Hydroxyl" or "hydroxy" refer to the group —OH.

"Thiol" refers to the group —SH.

"Lower alkyl" alone or in combination means an alkane-derived radical containing from 1 to 6 carbon atoms (unless specifically defined) that includes a straight chain alkyl or branched alkyl. The straight chain or branched lower alkyl group is chemically feasible and attached at any available point to provide a stable compound. In many embodiments, a lower alkyl is a straight or branched alkyl group containing from 1-6, 1-4, or 1-2, carbon atoms, such as methyl, ethyl, propyl, isopropyl, butyl, t-butyl, and the like. A lower alkyl may be independently substituted as described herein, unless indicated otherwise, with one or more, preferably 1, 2, 3, 4 or 5, also 1, 2, or 3 substituents, wherein the substituents are as indicated. For example "fluoro substituted lower alkyl" denotes a lower alkyl group substituted with one or more fluoro atoms, such as perfluoroalkyl, where preferably the lower alkyl is substituted with 1, 2, 3, 4 or 5 fluoro atoms, also 1, 2, or 3 fluoro atoms. It is understood that any such substitutions, or substitution of lower alkyl on another moiety, are chemically feasible and attached at any available atom to provide a stable compound.

"Lower alkylene" means a divalent alkane derived radical containing from 1 to 6 carbon atoms (unless specifically defined). In many embodiments, a lower alkylene is a methylene, ethylene, propylene, or the like.

"Lower alkenyl" alone or in combination means a straight or branched hydrocarbon containing 2-6 carbon atoms (unless specifically defined) and at least one, preferably 1-3, more preferably 1-2, most preferably one, carbon to carbon double bond. Carbon to carbon double bonds may be either contained within a straight chain or branched portion. The straight chain or branched lower alkenyl group is chemically feasible and attached at any available point to provide a stable compound. Examples of lower alkenyl groups include ethenyl, propenyl, isopropenyl, butenyl, and the like. A "substituted lower alkenyl" denotes lower alkenyl that is independently substituted, unless indicated otherwise, with one or more, preferably 1, 2, 3, 4 or 5, also 1, 2, or 3 substituents, wherein the substituents are as indicated. For example "lower alkenyl optionally substituted with C(O)—O—$R^{28}$" denotes a lower alkenyl group that may be substituted with a carboxylic acid moiety, i.e. C(O)—O—$R^{28}$ is substituted on the alkenyl group, where the carbon of C(O)—O—$R^{28}$ is bound to a carbon of the alkenyl group. It is understood that any such substitutions, or substitution of lower alkenyl on another moiety, are chemically feasible and attached at any available atom to provide a stable compound.

"Lower alkynyl" alone or in combination means a straight or branched hydrocarbon containing 2-6 carbon atoms (unless specifically defined) containing at least one, preferably one, carbon to carbon triple bond. The straight chain or branched lower alkynyl group is chemically feasible and attached at any available point to provide a stable compound. Examples of alkynyl groups include ethynyl, propynyl, butynyl, and the like. A "substituted lower alkynyl" denotes lower alkynyl that is independently substituted, unless indicated otherwise, with one or more, preferably 1, 2, 3, 4 or 5, also 1, 2, or 3 substituents, wherein the substituents are as indicated. For example "lower alkynyl optionally substituted with $R^9$" denotes a lower alkynyl group that may be substituted with a substituent $R^9$. It is understood that any such substitutions, or substitution of lower alkynyl on another moiety, are chemically feasible and attached at any available atom to provide a stable compound.

"Cycloalkyl" refers to saturated or unsaturated, non-aromatic monocyclic carbon ring systems of 3-10, also 3-8, more preferably 3-6, ring members per ring, such as cyclopropyl, cyclopentyl, cyclohexyl, cycloheptyl, and the like. A "substituted cycloalkyl" is a cycloalkyl that is independently substituted, unless indicated otherwise, with one or more, preferably 1, 2, 3, 4 or 5, also 1, 2, or 3 substituents, wherein the substituents are as indicated. It is understood that substitutions on cycloalkyl, or substitution of cycloalkyl on another moiety, are chemically feasible and attached at any available atom to provide a stable compound.

"Heterocycloalkyl" refers to a saturated or unsaturated non-aromatic cycloalkyl group having from 5 to 10 atoms in which from 1 to 3 carbon atoms in the ring are replaced by heteroatoms of O, S or N, and are optionally fused with benzo or heteroaryl of 5-6 ring members. Heterocycloalkyl is also intended to include oxidized S or N, such as sulfinyl, sulfonyl and N-oxide of a tertiary ring nitrogen. Heterocycloalkyl is also intended to include compounds in which a ring carbon may be oxo substituted, i.e. the ring carbon is a carbonyl group, such as lactones and lactams. The point of attachment of the heterocycloalkyl ring is at a carbon or nitrogen atom such that a stable ring is retained. Examples of heterocycloalkyl groups include, but are not limited to, morpholino, tetrahydrofuranyl, dihydropyridinyl, piperidinyl, pyrrolidinyl, pyrrolidonyl, piperazinyl, dihydrobenzofuryl, and dihydroindolyl. A "substituted heterocycloalkyl" is a heterocycloalkyl that is independently substituted, unless indicated otherwise, with one or more, preferably 1, 2, 3, 4 or 5, also 1, 2, or 3 substituents, wherein the substituents are as indicated. It is understood that substitutions on heterocycloalkyl, or substitution of heterocycloalkyl on another moiety, are chemically feasible and attached at any available atom to provide a stable compound.

"Aryl" alone or in combination refers to a monocyclic or bicyclic ring system containing aromatic hydrocarbons such as phenyl or naphthyl, which may be optionally fused with a cycloalkyl of preferably 5-7, more preferably 5-6, ring members. A "substituted aryl" is an aryl that is independently substituted, unless indicated otherwise, with one or more, preferably 1, 2, 3, 4 or 5, also 1, 2, or 3 substituents, wherein the substituents are as indicated. It is understood that substitutions on aryl, or substitution of aryl on another moiety, are chemically feasible and attached at any available atom to provide a stable compound.

"Heteroaryl" alone or in combination refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is provided. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl. A "substituted heteroaryl" is a heteroaryl that is independently substituted, unless indicated otherwise, with one or more, preferably 1, 2, 3, 4 or 5, also 1, 2, or 3 substituents, wherein the substituents are as indicated. It is understood that substitutions on heteroaryl, or substitution of heteroaryl on another moiety, are chemically feasible and attached at any available atom to provide a stable compound.

"Lower alkoxy" denotes the group —$OR^a$, where $R^a$ is lower alkyl. "Substituted lower alkoxy" denotes lower alkoxy in which $R^a$ is lower alkyl substituted with one or more substituents as indicated herein. Preferably, substitution of lower alkoxy is with 1, 2, 3, 4, or 5 substituents, also 1, 2, or 3 substituents. For example "fluoro substituted lower alkoxy" denotes lower alkoxy in which the lower alkyl is substituted with one or more fluoro atoms, where preferably the lower alkoxy is substituted with 1, 2, 3, 4 or 5 fluoro atoms, also 1, 2, or 3 fluoro atoms. It is understood that substitutions on alkoxy, or substitution of alkoxy on another moiety, are chemically feasible and attached at any available atom to provide a stable compound.

"Lower alkylthio" denotes the group —$SR^b$, where $R^b$ is lower alkyl. "Substituted lower alkylthio" denotes lower alkylthio in which $R^b$ is lower alkyl substituted with one or more substituents as indicated herein. Preferably, substitution of lower alkylthio is with 1, 2, 3, 4, or 5 substituents, also 1, 2, or 3 substituents. For example "fluoro substituted lower alkylthio" denotes lower alkylthio in which the lower alkyl is substituted with one or more fluoro atoms, where preferably the lower alkylthio is substituted with 1, 2, 3, 4 or 5 fluoro atoms, also 1, 2, or 3 fluoro atoms. It is understood that substitutions on alkylthio, or substitution of alkylthio on another moiety, are chemically feasible and attached at any available atom to provide a stable compound.

"Mono-alkylamino" denotes the group —$NHR^c$ where $R^c$ is lower alkyl. "Di-alkylamino" denotes the group —$NR^cR^d$, where $R^c$ and $R^d$ are independently lower alkyl. "Cycloalkylamino" denotes the group —$NR^eR^f$, where $R^e$ and $R^f$ combine with the nitrogen to form a 5-7 membered heterocycloalkyl, where the heterocycloalkyl may contain an additional heteroatom within the ring, such as O, N, or S, and may also be further substituted with lower alkyl. Examples of 5-7 membered heterocycloalkyl include, but are not limited to, piperidine, piperazine, 4-methylpiperazine, morpholine, and thiomorpholine. It is understood that when mono-alkylamino, di-alkylamino, or cycloalkylamino are substituents on other moieties, these are chemically feasible and attached at any available atom to provide a stable compound.

As used herein, the terms "treat", "treating", "therapy", "therapies", and like terms refer to the administration of material, e.g., any one or more compound(s) as described herein in an amount effective to prevent, alleviate, or ameliorate one or more symptoms of a disease or condition, i.e., indication, and/or to prolong the survival of the subject being treated.

As used herein, the term "solid form" refers to a solid preparation (i.e. a preparation that is neither gas nor liquid) of a pharmaceutically active compound that is suitable for administration to an intended animal subject for therapeutic purposes. The solid form includes any complex, such as a salt, co-crystal or an amorphous complex, as well as any polymorph of the compound. The solid form may be substantially crystalline, semi-crystalline or substantially amorphous. The solid form may be administered directly or used in the preparation of a suitable composition having improved pharmaceutical properties. For example, the solid form may be used in a formulation comprising at least one pharmaceutically acceptable carrier or excipient.

As used herein, the term "substantially crystalline" material embraces material which has greater than about 90% crystallinity; and "crystalline" material embraces material which has greater than about 98% crystallinity.

As used herein, the term "substantially amorphous" material embraces material which has no more than about 10% crystallinity; and "amorphous" material embraces material which has no more than about 2% crystallinity.

As used herein, the term "semi-crystalline" material embraces material which is greater than 10% crystallinity, but no greater than 90% crystallinity; preferably "semi-crystalline" material embraces material which is greater than 20% crystallinity, but no greater than 80% crystallinity. In one aspect of the present invention, a mixture of solid forms of a compound may be prepared, for example, a mixture of amorphous and crystalline solid forms, e.g. to provide a "semi-crystalline" solid form. Such a "semi-crystalline" solid form may be prepared by methods known in the art, for example by mixing an amorphous solid form with a crystalline solid form in the desired ratio. In some instances, a compound mixed with acid or base forms an amorphous complex; a semi-crystalline solid can be prepared employing an amount of compound component in excess of the stoichiometry of the compound and acid or base in the amorphous complex, thereby resulting in an amount of the amorphous complex that is based on the stoichiometry thereof, with excess compound in a crystalline form. The amount of excess compound used in the preparation of the complex can be adjusted to provide the desired ratio of amorphous complex to crystalline compound in the resulting mixture of solid forms. For example, where the amorphous complex of acid or base and compound has a 1:1 stoichiometry, preparing said complex with a 2:1 mole ratio of compound to acid or base will result in a solid form of 50% amorphous complex and 50% crystalline compound. Such a mixture of solid forms may be beneficial as a drug product, for example, by providing an amorphous component having improved biopharmaceutical properties along with the crystalline component. The amorphous component would be more readily bioavailable while the crystalline component would have a delayed bioavailablity. Such a mixture may provide both rapid and extended exposure to the active compound.

As used herein, the term "complex" refers to a combination of a pharmaceutically active compound and an additional molecular species that forms or produces a new chemical species in a solid form. In some instances, the complex may be a salt, i.e. where the additional molecular species provides an acid/base counter ion to an acid/base group of the compound resulting in an acid:base interaction that forms a typical salt. While such salt forms are typically substantially crystalline, they can also be partially crystalline, substantially amorphous, or amorphous forms. In some instances, the additional molecular species, in combination with the pharmaceutically active compound, forms a non-salt co-crystal, i.e. the compound and molecular species do not interact by way of a typical acid:base interaction, but still form a substantially crystalline structure. Co-crystals may also be formed from a salt of the compound and an additional molecular species. In some instances, the complex is a substantially amorphous complex, which may contain salt-like acid:base interactions that do not form typical salt crystals, but instead form a substantially amorphous solid, i.e. a solid whose X-ray powder diffraction pattern exhibits no sharp peaks (e.g. exhibits an amorphous halo).

As used herein, the term "stoichiometry" refers to the molar ratio of a combination of two or more components, for example, the molar ratio of acid or base to compound that form an amorphous complex. For example, a 1:1 mixture of acid or base with compound (i.e. 1 mole acid or base per mole of compound) resulting in an amorphous solid form has a 1:1 stoichiometry.

As used herein, the term "composition" refers to a pharmaceutical preparation suitable for administration to an intended subject for therapeutic purposes that contains at least one pharmaceutically active compound, including any solid form thereof. The composition may include at least one pharmaceutically acceptable component to provide an improved formulation of the compound, such as a suitable carrier or excipient.

As used herein, the term "subject" refers to a living organism that is treated with compounds as described herein, including, but not limited to, any mammal, such as a human, other primates, sports animals, animals of commercial interest such as cattle, farm animals such as horses, or pets such as dogs and cats.

As used herein, the term "biopharmaceutical properties" refers to the pharmacokinetic action of a compound or complex of the present invention, including the dissolution, absorption and distribution of the compound on administration to a subject. As such, certain solid forms of compounds of the invention, such as amorphous complexes of compounds of the invention, are intended to provide improved dissolution and absorption of the active compound, which is typically reflected in improved $C_{max}$ (i.e. the maximum achieved concentration in the plasma after administration of the drug) and improved AUC (i.e. area under the curve of drug plasma concentration vs. time after administration of the drug).

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated.

In the present context, the terms "synergistically effective" or "synergistic effect" indicate that two or more compounds that are therapeutically effective, when used in combination, provide improved therapeutic effects greater than the additive effect that would be expected based on the effect of each compound used by itself.

By "assaying" is meant the creation of experimental conditions and the gathering of data regarding a particular result of the exposure to specific experimental conditions. For example, enzymes can be assayed based on their ability to act upon a detectable substrate. A compound can be assayed based on its ability to bind to a particular target molecule or molecules.

As used herein, the term "modulating" or "modulate" refers to an effect of altering a biological activity (i.e. increasing or decreasing the activity), especially a biological activity associated with a particular biomolecule such as a protein kinase. For example, an inhibitor of a particular biomolecule modulates the activity of that biomolecule, e.g., an enzyme, by decreasing the activity of the biomolecule, such as an enzyme. Such activity is typically indicated in terms of an inhibitory concentration ($IC_{50}$) of the compound for an inhibitor with respect to, for example, an enzyme.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

"Pain" or a "pain condition" can be acute and/or chronic pain, including, without limitation, arachnoiditis; arthritis (e.g. osteoarthritis, rheumatoid arthritis, ankylosing spondylitis, gout); back pain (e.g. sciatica, ruptured disc, spondylolisthesis, radiculopathy); burn pain; cancer pain; dysmenorrhea; headaches (e.g. migraine, cluster headaches, tension headaches); head and facial pain (e.g. cranial neuralgia, trigeminal neuralgia); hyperalgesia; hyperpathia; inflammatory pain (e.g. pain associated with irritable bowel syndrome, inflammatory bowel disease, ulcerative colitis, Crohn's disease, cystitis, pain from bacterial, fungal or viral infection); keloid or scar tissue formation; labor or delivery pain; muscle pain (e.g. as a result of polymyositis, dermatomyositis, inclusion body myositis, repetitive stress injury (e.g. writer's cramp, carpal tunnel syndrome, tendonitis, tenosynovitis)); myofascial pain syndromes (e.g. fibromyalgia); neuropathic pain (e.g. diabetic neuropathy, causalgia, entrapment neuropathy, brachial plexus avulsion, occipital neuralgia, gout, reflex sympathetic dystrophy syndrome, phantom limb or post-amputation pain, postherpetic neuralgia, central pain syndrome, or nerve pain resulting from trauma (e.g. nerve injury), disease (e.g. diabetes, multiple sclerosis, Guillan-Barre Syndrome, myasthenia gravis, neurodegenerative diseases such as Parkinson's disease, Alzheimer's disease, amyotrophic lateral sclerosis, or cancer treatment); pain associated with skin disorders (e.g. shingles, herpes simplex, skin tumors, cysts, neurofibromatosis); sports injuries (e.g. cuts, sprains, strains, bruises, dislocations, fractures, spinal chord, head); spinal stenosis; surgical pain; tactile allodynia; temporomandibular disorders; vascular disease or injury (e.g. vasculitis, coronary artery disease, reperfusion injury (e.g. following ischemia, stroke, or myocardial infarcts)); other specific organ or tissue pain (e.g. ocular pain, corneal pain, bone pain, heart pain, visceral pain (e.g. kidney, gallbladder, gastrointestinal), joint pain, dental pain, pelvic hypersensitivity, pelvic pain, renal colic, urinary incontinence); other disease associated pain (e.g. sickle cell anemia, AIDS, herpes zoster, psoriasis, endometriosis, asthma, chronic obstructive pulmonary disease (COPD), silicosis, pulmonary sarcoidosis, esophagitis, heart burn, gastroesophageal reflux disorder, stomach and duodenal ulcers, functional dyspepsia, bone resorption disease, osteoporosis, cerebral malaria, bacterial meningitis); or pain due to graft v. host rejection or allograft rejections.

Kinase Activity Assays

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases describe assays that can be used.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phosphor-specific antibody.

Organic Synthetic Techniques

A wide array of organic synthetic techniques exist in the art to facilitate the construction of potential modulators. Many of these organic synthetic methods are described in detail in standard reference sources utilized by those skilled in the art. One example of such a reference is March, 1994, *Advanced Organic Chemistry; Reactions, Mechanisms and Structure*, New York, McGraw Hill. Thus, the techniques useful to synthesize a potential modulator of kinase function are readily available to those skilled in the art of organic chemical synthesis.

Alternative Compound Forms or Derivatives

Compounds contemplated herein are described with reference to both generic formulae and specific compounds. In addition, invention compounds may exist in a number of different forms or derivatives, all within the scope of the present invention. Alternative forms or derivatives, include, for example, (a) prodrugs, and active metabolites (b) tautomers, isomers (including stereoisomers and regioisomers), and racemic mixtures (c) pharmaceutically acceptable salts and (d) solid forms, including different crystal forms, polymorphic or amorphous solids, including hydrates and solvates thereof, and other forms.

(a) Prodrugs and Metabolites

In addition to the present formulae and compounds described herein, the invention also includes prodrugs (generally pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more advantageous handling, administration, and/or metabolic properties. For example, some prodrugs are esters of the active compound; during metabolysis, the ester group is cleaved to yield the active drug. Esters include, for example, esters of a carboxylic acid group, or S-acyl or O-acyl derivatives of thiol, alcohol, or phenol groups. In this context, a common example is an alkyl ester of a carboxylic acid. Prodrugs may also include variants wherein an —NH group of the compound has undergone acylation, such as the 7-position of the pyrrolo[2,3-d]pyrimidine ring, the 1-position of the 1H-pyrrolo[2,3-b]pyridine ring, or the nitrogen of the sulfonamide group of compounds as described herein, where cleavage of the acyl group provides the free —NH group of the active drug. Some prodrugs are activated enzymatically to yield the active compound, or a compound may undergo further chemical reaction to yield the active compound. Prodrugs may proceed from prodrug form to active form in a single step or may have one or more intermediate forms which may themselves have activity or may be inactive.

As described in *The Practice of Medicinal Chemistry*, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the following types:

Oxidative reactions: Oxidative reactions are exemplified without limitation by reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive reactions: Reductive reactions are exemplified without limitation by reactions such as reduction of carbonyl functionalitites, reduction of alcohol functionalities and carbon-carbon double bonds, reduction of nitrogen-containing functional groups, and other reduction reactions.

Reactions without change in the oxidation state: Reactions without change in the state of oxidation are exemplified without limitation by reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 20040077595, application Ser. No. 10/656,838, incorporated herein by reference.) Such carrier prodrugs are often advantageous for orally administered drugs. In some instances, the transport moiety provides targeted delivery of the drug, for example the drug may be conjugated to an antibody or antibody fragment. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, supra.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic processes in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug. For example, in some compounds, one or more alkoxy groups can be metabolized to hydroxyl groups while retaining pharmacologic activity and/or carboxyl groups can be esterified, e.g., glucuronidation. In some cases, there can be more than one metabolite, where an intermediate metabolite(s) is further metabolized to provide an active metabolite. For example, in some cases a derivative compound resulting from metabolic glucuronidation may be inactive or of low activity, and can be further metabolized to provide an active metabolite.

Metabolites of a compound may be identified using routine techniques known in the art, and their activities determined using tests such as those described herein. See, e.g., Bertolini et al., 1997, *J. Med. Chem.*, 40:2011-2016; Shan et al., 1997, *J Pharm Sci* 86(7):756-757; Bagshawe, 1995, *Drug Dev. Res.*, 34:220-230; Wermuth, supra.

(b) Tautomers, Stereoisomers, and Regioisomers

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds according to the present invention may exist as stereoisomers, i.e. having the same atomic connectivity of covalently bonded atoms yet differing in the spatial orientation of the atoms. For example, compounds may be optical stereoisomers, which contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or mixtures of enantiomers and/or diastereomers. As another example, stereoisomers include geometric isomers, such as cis- or trans-orientation of substituents on adjacent carbons of a double bond. All such single stereoisomers, racemates and mixtures thereof are intended to be within the scope of the present invention. Unless specified to the contrary, all such stereoisomeric forms are included within the formulae provided herein.

In some embodiments, a chiral compound of the present invention is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form, such optically pure form being prepared and/or isolated by methods known in the art (e.g. by recrystallization techniques, chiral synthetic techniques (including synthesis from optically pure starting materials), and chromatographic separation using a chiral column.

(c) Pharmaceutically Acceptable Salts

Unless specified to the contrary, specification of a compound herein includes pharmaceutically acceptable salts of such compound. Thus, compounds described herein can be in the form of pharmaceutically acceptable salts, or can be formulated as pharmaceutically acceptable salts. Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug. A compound of the invention may possess a sufficiently acidic, a sufficiently basic, or both functional groups, and accordingly can react with any of a number of inorganic or organic bases, and inorganic and organic acids, to form a pharmaceutically acceptable salt.

Pharmaceutically acceptable salts include acid addition salts such as those containing chloride, bromide, iodide, hydrochloride, acetate, phenylacetate, acrylate, ascorbate, aspartate, benzoate, 2-phenoxybenzoate, 2-acetoxybenzoate, dinitrobenzoate, hydroxybenzoate, methoxybenzoate, methylbenzoate, bicarbonate, butyne-1,4 dioate, hexyne-1,6-dioate, caproate, caprylate, chlorobenzoate, cinnamate, citrate, decanoate, formate, fumarate, glycolate, gluconate, glucarate, glucuronate, glucose-6-phosphate, glutamate, heptanoate, hexanoate, isethionate, isobutyrate, gamma-hydroxybutyrate, phenylbutyrate, lactate, malate, maleate, hydroxymaleate, methylmaleate, malonate, mandelate, nicotinate, nitrate, isonicotinate, octanoate, oleate, oxalate, pamoate, phosphate, monohydrogenphosphate, dihydrogenphosphate, orthophosphate, metaphosphate, pyrophosphate, 2-phosphoglycerate, 3-phosphoglycerate, phthalate, propionate, phenylpropionate, propiolate, pyruvate, quinate, salicylate, 4-aminosalicylate, sebacate, stearate, suberate, succinate, sulfate, pyrosulfate, bisulfate, sulfite, bisulfite, sulfamate, sulfonate, benzenesulfonate (i.e. besylate), ethanesulfonate (i.e. esylate), ethane-1,2-disulfonate, 2-hydroxyethanesulfonate (i.e. isethionate), methanesulfonate (i.e. mesylate), naphthalene-1-sulfonate, naphthalene-2-sulfonate (i.e. napsylate), propanesulfonate, p-toluenesulfonate (i.e. tosylate), xylenesulfonates, cyclohexylsulfamate, tartrate, and trifluoroacetate. These pharmaceutically acceptable acid addition salts can be prepared using the appropriate corresponding acid.

When acidic functional groups, such as carboxylic acid or phenol are present, pharmaceutically acceptable salts also include basic addition salts such as those containing benzathine, chloroprocaine, choline, ethanolamine, diethanolamine, triethanolamine, t-butylamine, dicyclohexylamine, ethylenediamine, N,N'-dibenzylethylenediamine, meglumine, hydroxyethylpyrrolidine, piperidine, morpholine, piperazine, procaine, aluminum, calcium, copper, iron, lithium, magnesium, manganese, potassium, sodium, zinc, ammonium, and mono-, di-, or tri-alkylamines (e.g. diethylamine), or salts derived from amino acids such as L-histidine, L-glycine, L-lysine, and L-arginine. For example, see *Remington's Pharmaceutical Sciences*, 19th ed., Mack Publishing Co., Easton, Pa., Vol. 2, p. 1457, 1995. These pharmaceutically acceptable base addition salts can be prepared using the appropriate corresponding base.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent. If the particular compound is an acid, the desired pharmaceutically acceptable salt may be prepared by any suitable method, for example, treatment of the free acid with an appropriate inorganic or organic base.

(d) Other Compound Forms

In the case of agents that are solids, it is understood by those skilled in the art that the compounds and salts may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the present invention and specified formulae. Whereas salts are formed by acid/base addition, i.e. a free base or free acid of the compound of interest forms an acid/base reaction with a corresponding addition base or addition acid, respectively, resulting in an ionic charge interaction, co-crystals are a new chemical species that is formed between neutral compounds, resulting in the compound and an additional molecular species in the same crystal structure.

In some instances, compounds of the invention are complexed with an acid or a base, including base addition salts such as ammonium, diethylamine, ethanolamine, ethylenediamine, diethanolamine, t-butylamine, piperazine, meglumine; acid addition salts, such as acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In combining the compound of the invention with the acid or base, an amorphous complex is preferably formed rather than a crystalline material such as a typical salt or co-crystal. In some instances, the amorphous form of the complex is facilitated by additional processing, such as by spray-drying, mechanochemical methods such as roller compaction, or microwave irradiation of the parent compound mixed with the acid or base. Such methods may also include addition of ionic and/or non-ionic polymer systems, including, but not limited to, hydroxypropyl methyl cellulose acetate succinate (HPMCAS) and methacrylic acid copolymer (e.g. Eudragit® L100-55), that further stabilize the amorphous nature of the complex. Such amorphous complexes provide several advantages. For example, lowering of the melting temperature relative to the free base facilitates additional processing, such as hot melt extrusion, to further improve the biopharmaceutical properties of the compound. Also, the amorphous complex is readily friable, which provides improved compression for loading of the solid into capsule or tablet form.

Additionally, the formulae are intended to cover hydrated or solvated as well as unhydrated or unsolvated forms of the identified structures. For example, the indicated compounds include both hydrated and non-hydrated forms. Other examples of solvates include the structures in combination with a suitable solvent, such as isopropanol, ethanol, methanol, dimethyl sulfoxide, ethyl acetate, acetic acid, or ethanolamine.

Formulations and Administration

The methods and compounds will typically be used in therapy for human subjects. However, they may also be used to treat similar or identical indications in other animal subjects. Compounds described herein can be administered by different routes, including injection (i.e. parenteral, including intravenous, intraperitoneal, subcutaneous, and intramuscular), oral, transdermal, transmucosal, rectal, or inhalant. Such dosage forms should allow the compound to reach target cells. Other factors are well known in the art, and include considerations such as toxicity and dosage forms that retard the compound or composition from exerting its effects. Techniques and formulations generally may be found in *Remington: The Science and Practice of Pharmacy,* 21$^{st}$ edition, Lippincott, Williams and Wilkins, Philadelphia, Pa., 2005 (hereby incorporated by reference herein).

In some embodiments, compositions will comprise pharmaceutically acceptable carriers or excipients, such as fillers, binders, disintegrants, glidants, lubricants, complexing agents, solubilizers, and surfactants, which may be chosen to facilitate administration of the compound by a particular route. Examples of carriers include calcium carbonate, calcium phosphate, various sugars such as lactose, glucose, or sucrose, types of starch, cellulose derivatives, gelatin, lipids, liposomes, nanoparticles, and the like. Carriers also include physiologically compatible liquids as solvents or for suspensions, including, for example, sterile solutions of water for injection (WFI), saline solution, dextrose solution, Hank's solution, Ringer's solution, vegetable oils, mineral oils, animal oils, polyethylene glycols, liquid paraffin, and the like. Excipients may also include, for example, colloidal silicon dioxide, silica gel, talc, magnesium silicate, calcium silicate, sodium aluminosilicate, magnesium trisilicate, powdered cellulose, macrocrystalline cellulose, carboxymethyl cellulose, cross-linked sodium carboxymethylcellulose, sodium benzoate, calcium carbonate, magnesium carbonate, stearic acid, aluminum stearate, calcium stearate, magnesium stearate, zinc stearate, sodium stearyl fumarate, syloid, stearowet C, magnesium oxide, starch, sodium starch glycolate, glyceryl monostearate, glyceryl dibehenate, glyceryl palmitostearate, hydrogenated vegetable oil, hydrogenated cotton seed oil, castor seed oil mineral oil, polyethylene glycol (e.g. PEG 4000-8000), polyoxyethylene glycol, poloxamers, povidone, crospovidone, croscarmellose sodium, alginic acid, casein, methacrylic acid divinylbenzene copolymer, sodium docusate, cyclodextrins (e.g. 2-hydroxypropyl-.delta.-cyclodextrin), polysorbates (e.g. polysorbate 80), cetrimide, TPGS (d-alpha-tocopheryl polyethylene glycol 1000 succinate), magnesium lauryl sulfate, sodium lauryl sulfate, polyethylene glycol ethers, di-fatty acid ester of polyethylene glycols, or a polyoxyalkylene sorbitan fatty acid ester (e.g., polyoxyethylene sorbitan ester Tween®), polyoxyethylene sorbitan fatty acid esters, sorbitan fatty acid ester, e.g. a sorbitan fatty acid ester from a fatty acid such as oleic, stearic or palmitic acid, mannitol, xylitol, sorbitol, maltose, lactose, lactose monohydrate or lactose spray dried, sucrose, fructose, calcium phosphate, dibasic calcium phosphate, tribasic calcium phosphate, calcium sulfate, dextrates, dextran, dextrin, dextrose, cellulose acetate, maltodextrin, simethicone, polydextrosem, chitosan, gelatin, HPMC (hydroxypropyl methyl celluloses), HPC (hydroxypropyl cellulose), hydroxyethyl cellulose, and the like.

In some embodiments, oral administration may be used. Pharmaceutical preparations for oral use can be formulated into conventional oral dosage forms such as capsules, tablets, and liquid preparations such as syrups, elixirs, and concentrated drops. Compounds described herein may be combined with solid excipients, optionally grinding a resulting mixture, and processing the mixture of granules, after adding suitable auxiliaries, if desired, to obtain, for example, tablets, coated tablets, hard capsules, soft capsules, solutions (e.g. aqueous, alcoholic, or oily solutions) and the like. Suitable excipients are, in particular, fillers such as sugars, including lactose, glucose, sucrose, mannitol, or sorbitol; cellulose preparations, for example, corn starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone); oily excipients, including vegetable and animal oils, such as sunflower oil, olive oil, or codliver oil. The oral dosage formulations may also contain disintegrating agents, such as the cross-linked polyvinylpyrrolidone, agar, or alginic acid, or a salt thereof such as sodium alginate; a lubricant, such as talc or magnesium stearate; a plasticizer, such as glycerol or sorbitol; a sweetening such as sucrose, fructose, lactose, or aspartame; a natural or artificial flavoring agent, such as peppermint, oil of wintergreen, or cherry flavoring; or dye-stuffs or pigments, which may be used for identification or characterization of different doses or combinations. Also provided are dragee cores with suitable coatings. For this purpose, concentrated sugar solutions may be used, which may optionally contain, for example, gum arabic, talc, polyvinylpyrrolidone, carbopol gel, polyethylene glycol, and/or titanium dioxide, lacquer solutions, and suitable organic solvents or solvent mixtures.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols.

In some embodiments, injection (parenteral administration) may be used, e.g., intramuscular, intravenous, intraperitoneal, and/or subcutaneous. Compounds described herein for injection may be formulated in sterile liquid solutions, preferably in physiologically compatible buffers or solutions, such as saline solution, Hank's solution, or Ringer's solution. Dispersions may also be prepared in non-aqueous solutions, such as glycerol, propylene glycol, ethanol, liquid polyethylene glycols, triacetin, and vegetable oils. Solutions may also contain a preservative, such as methylparaben, propylparaben, chlorobutanol, phenol, sorbic acid, thimerosal, and the like. In addition, the compounds may be formulated in solid form, including, for example, lyophilized forms, and redissolved or suspended prior to use.

In some embodiments, transmucosal, topical or transdermal administration may be used. In such formulations of compounds described herein, penetrants appropriate to the barrier to be permeated are used. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal). Compositions of compounds described herein for topical administration may be formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In some embodiments, carriers are selected such that the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount of solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will be continuous rather than intermittent throughout the dosage regimen.

In some embodiments, compounds are administered as inhalants. Compounds described herein may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds described herein may also be used in combination with other inhaled therapies, for example corticosteroids such as fluticasone proprionate, beclomethasone dipropionate, triamcinolone acetonide, budesonide, and mometasone furoate; beta agonists such as albuterol, salmeterol, and formoterol; anticholinergic agents such as ipratropium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

The amounts of various compounds to be administered can be determined by standard procedures taking into account factors such as the compound activity (in vitro, e.g. the compound $IC_{50}$ vs. target, or in vivo activity in animal efficacy models), pharmacokinetic results in animal models (e.g. biological half-life or bioavailability), the age, size, and weight of the subject, and the disorder associated with the subject. The importance of these and other factors are well known to those of ordinary skill in the art. Generally, a dose will be in the range of about 0.01 to 50 mg/kg, also about 0.1 to 20 mg/kg of the subject being treated. Multiple doses may be used.

The compounds described herein may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the invention or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound described herein, or at the same time as a compound described herein. Use in combination also includes use with a therapy or medical procedure that is administered once or infrequently, such as surgery, along with a compound described herein administered within a short time or longer time before or after the other therapy or procedure. In some embodiments, the present invention provides for delivery of a compound described herein and one or more other drug therapeutics delivered by a different route of administration or by the same route of administration. The use in combination for any route of administration includes delivery of a compound described herein and one or more other drug therapeutics delivered by the same route of administration together in any formulation, including formulations where the two compounds are chemically linked in such a way that they maintain their therapeutic activity when administered. In one aspect, the other drug therapy may be co-administered with a compound described herein. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of a compound described herein and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

EXAMPLES

Examples related to the present invention are described below. In most cases, alternative techniques can be used. The examples are intended to be illustrative and are not limiting or restrictive to the scope of the invention. For example, where additional compounds are prepared following a protocol of a Scheme for a particular compound, it is understood that conditions may vary, for example, any of the solvents, reaction times, reagents, temperatures, work up conditions, or other reaction parameters may be varied employing alternate solvents, reagents, reaction times, temperatures, work up conditions, and the like, as are readily available to one skilled in the art. In some examples, the mass spectrometry result indicated for a compound may have more than one value due to the isotope distribution of an atom in the molecule, such as a compound having a bromo or chloro substituent.

Example 1

A compound having the structure of Compound 1a is synthesized. Compound 1a is tested in an assay for ZAP-70 kinase activity.

Example 2

A compound having the structure of Compound 1b is synthesized. Compound 1b is tested in an assay for ZAP-70 kinase activity.

Example 3

A compound having the structure of Compound 1c is synthesized. Compound 1a is tested in an assay for ZAP-70 kinase activity.

Example 4

A compound having the structure of Compound 2a is synthesized. Compound 2a is tested in an assay for ZAP-70 kinase activity.

Example 5

A compound having the structure of Compound 2b is synthesized. Compound 2b is tested in an assay for ZAP-70 kinase activity.

Example 6

A compound having the structure of Compound 2c is synthesized. Compound 2c is tested in an assay for ZAP-70 kinase activity.

Example 7

A compound having the structure of Compound 2d is synthesized. Compound 2d is tested in an assay for ZAP-70 kinase activity.

Example 8

A compound having the structure of Compound 3a is synthesized. Compound 3a is tested in an assay for ZAP-70 kinase activity.

Example 9

A compound having the structure of Compound 3b is synthesized. Compound 3b is tested in an assay for ZAP-70 kinase activity.

Example 10

A compound having the structure of Compound 3c is synthesized. Compound 3c is tested in an assay for ZAP-70 kinase activity.

Example 11

A compound having the structure of Compound 3d is synthesized. Compound 3d is tested in an assay for ZAP-70 kinase activity.

Example 12

A compound having the structure of Compound 4a is synthesized. Compound 4a is tested in an assay for ZAP-70 kinase activity.

Example 13

A compound having the structure of Compound 4b is synthesized. Compound 4b is tested in an assay for ZAP-70 kinase activity.

Example 14

A compound having the structure of Compound 4c is synthesized. Compound 4c is tested in an assay for ZAP-70 kinase activity.

Example 15

A compound having the structure of Compound 4d is synthesized. Compound 4d is tested in an assay for ZAP-70 kinase activity.

Example 16

A compound having the structure of Compound 5a is synthesized. Compound 5a is tested in an assay for ZAP-70 kinase activity.

Example 17

A compound having the structure of Compound 5b is synthesized. Compound 5b is tested in an assay for ZAP-70 kinase activity.

Example 18

A compound having the structure of Compound 5c is synthesized. Compound 5c is tested in an assay for ZAP-70 kinase activity.

Example 19

A compound having the structure of Compound 5d is synthesized. Compound 5d is tested in an assay for ZAP-70 kinase activity.

Additional features of the complex can be used to demonstrate improved properties, such as comparison of the intrinsic dissolution rate of a similarly prepared substantially amorphous citrate complex or formulation thereof as compared to that of a crystalline form of the compound or similar formulation thereof in simulated gastric fluid (SGF) without enzyme and in simulated intestinal fluid (SIF). A pellet of test sample is dissolved in the appropriate fluid, and the UV absorbance as a function of time is measured at 254 nm (SGF) or 310 nm (SIF) and plotted.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. Thus, for an embodiment of the invention using one of the terms, the invention also includes another embodiment wherein one of these terms is replaced with another of these terms. In each embodiment, the terms have their established meaning. Thus, for example, one embodiment may encompass a method "comprising" a series of steps, another embodiment would encompass a method "consisting essentially of" the same steps, and a third embodiment would encompass a method "consisting of" the same steps. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

What is claimed is:

1. A compound having Formula I:

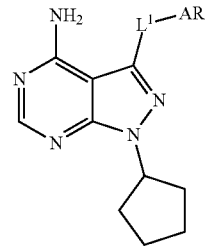

or a pharmaceutically acceptable salt thereof,
wherein:
(i) $L^1$ is selected from the group consisting of —CO—, $S(O)_2$ and —NH—; and
AR is phenyl substituted with one or more substituents selected from the group consisting of lower alkyl, lower alkoxy, and halogen; or
(ii) $L^1$ is selected from the group consisting of lower alkylene, —O—, —CO—, $S(O)_2$ and —NH—; and
AR is pyridinyl substituted with one or more substituents selected from the group consisting of lower alkyl, lower alkoxy, and halogen.

2. The compound of claim 1, wherein AR is pyridinyl, wherein the pyridinyl is substituted with from 1-3 groups independently selected from $CH_3$—, $CH_3O$—, F, Cl, Br or I.

3. The compound of claim 1, wherein AR is pyridinyl having the nitrogen at the position adjacent to the $L^1$ linkage.

4. The compound of claim 1, having Formula II:

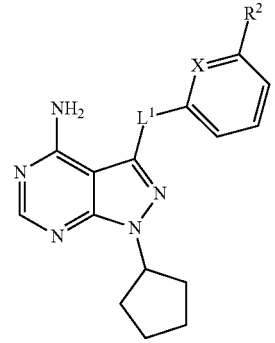

wherein:
(i) X is C; and
$L^1$ is selected from the group consisting of —CO—, $S(O)_2$ and —NH—; or
(ii) X is N; and
$L^1$ is selected from the group consisting of lower alkylene, —O—, —CO—, $S(O)_2$ and —NH—;
$R^2$ is selected from the group consisting of lower alkyl, lower alkoxy and halogen.

5. The compound of claim 1, wherein the compound is selected from the group consisting of:
(1-cyclopentyl-3-((6-methylpyridin-2-yl)methyl)-1H-pyrazolo[3,4-d]pyrimidin-4-amine),
(3-((6-chloropyridin-2-yl)methyl)-1-cyclopentyl-1H-pyrazolo[3,4-d]pyrimidin-4-amine),
(1-cyclopentyl-3-((6-fluoropyridin-2-yl)methyl)-1H-pyrazolo[3,4-d]pyrimidin-4-amine),
(1-cyclopentyl-3((6-methoxypyridin-2-yl)methyl)-1H-pyrazolo[3,4-d]pyrimidin-4-amine), (1-cyclopentyl-$N^3$-m-tolyl-1H-pyrazolo[3,4-d]pyrimidine-3,4-diamine),
($N^3$-(3-chlorophenyl)-1-cyclopentyl-1H-pyrazolo[3,4-d]pyrimidine-3,4-diamine),
(1-cyclopentyl-$N^3$-(3-fluorophenyl)-1H-pyrazolo[3,4-d]pyrimidine-3,4-diamine),
(1-cyclopentyl-$N^3$-(3-methoxyphenyl)-1H-pyrazolo[3,4-d]pyrimidine-3,4-diamine),
((4-amino-1-cyclopentyl-1H-pyrazolo[3,4-d]pyrimidin-3-yl)(m-tolyl)methanone),
((4-amino-1-cyclopentyl-1H-pyrazolo[3,4-d]pyrimidin-3-yl)(3-chlorophenyl)methanone) and
((4-amino-1-cyclopentyl-1H-pyrazolo[3,4-d]pyrimidin-3-yl)(3-fluorophenyl)methanone). ((4-amino-1-cyclopentyl-1H-pyrazolo[3,4-d]pyrimidin-3-yl)(3-fluorophenyl)methanone).

6. A pharmaceutical composition comprising a compound of claim 1 and a pharmaceutically acceptable carrier or excipient.

7. A pharmaceutical composition comprising a compound of claim 4 and a pharmaceutically acceptable carrier or excipient.

8. A pharmaceutical composition comprising a compound of claim 5 and a pharmaceutically acceptable carrier or excipient.

* * * * *